United States Patent [19]

Takaya et al.

[11] 4,427,677
[45] Jan. 24, 1984

[54] CEPHEM COMPOUNDS

[75] Inventors: Takao Takaya, Kawanishi; Hisashi Takasugi, Hamaguchinishi; Masayoshi Murata, Osaka; Akiteru Yoshioka, Kyoto, all of Japan

[73] Assignee: Fujisawa Pharmaceutical Co., Ltd., Osaka, Japan

[21] Appl. No.: 332,830

[22] Filed: Dec. 21, 1981

[30] Foreign Application Priority Data

Dec. 31, 1980 [GB] United Kingdom ................. 8041639
Jul. 13, 1981 [GB] United Kingdom ................. 8121557

[51] Int. Cl.³ ................. C07D 501/46; A61K 31/545
[52] U.S. Cl. ........................................ 424/246; 544/25
[58] Field of Search ........................... 544/25, 26, 27; 424/246

[56] References Cited

U.S. PATENT DOCUMENTS

| 4,258,041 | 3/1981 | O'Callaghan et al. | 424/246 |
| 4,278,671 | 7/1981 | Ochiai et al. | 424/246 |
| 4,329,453 | 5/1982 | Bropie et al. | 424/246 |

*Primary Examiner*—Nicholas S. Rizzo
*Attorney, Agent, or Firm*—Oblon, Fisher, Spivak, McClelland & Maier

[57] ABSTRACT

This invention relates to novel cephem compounds of high antimicrobial activity of the formula:

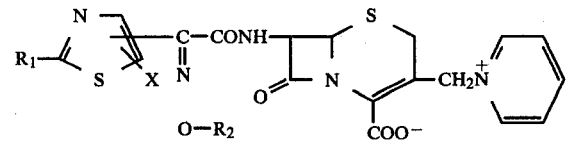

wherein
$R_1$ is amino, lower alkanoylamino or halo(lower)alkanoylamino,
$R_2$ is lower alkyl, lower alkylthio(lower)alkyl, lower alkenyl, lower alkynyl, carboxy(lower)alkyl or esterified carboxy(lower)alkyl, and
X is halogen;
and pharmaceutically acceptable salts thereof.

6 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compound is novel and can be represented by the following general formula (I).

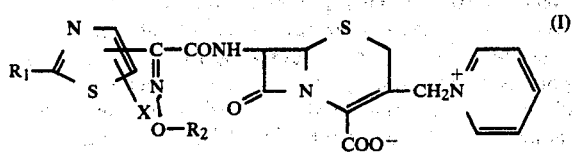

wherein
$R_1$ is amino or a protected amino group,
$R_2$ is aliphatic hydrocarbon group which may have suitable substituent(s), and
X is halogen.

According to the present invention, the object compound (I) can be prepared by the following processes.

Process A: N-Acylation

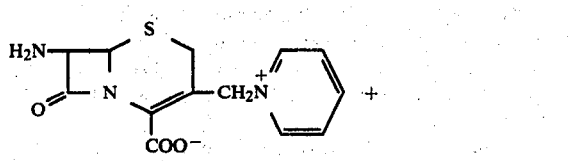

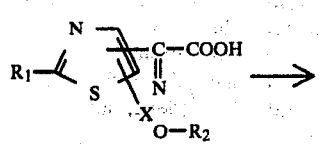

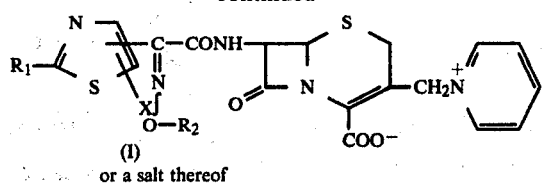

Process B: Elimination of amino-protective group

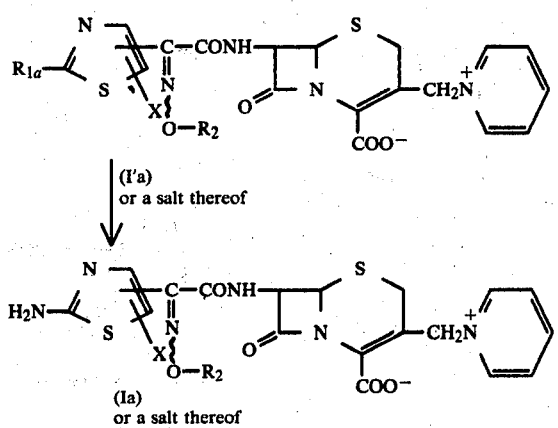

Process C: Elimination of carboxy-protective group

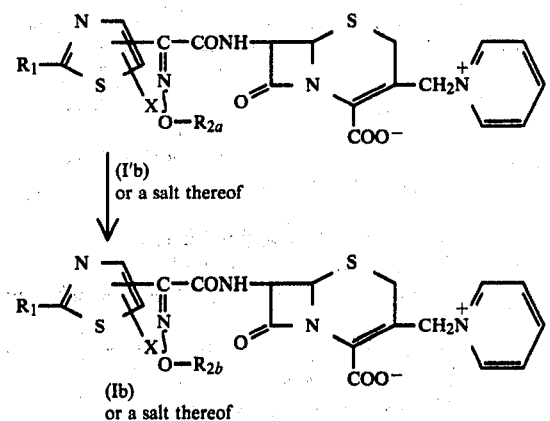

wherein
$R_1$, $R_2$ and X are each as defined above,
$R_{1a}$ is a protected amino group,
$R_{2a}$ is aliphatic hydrocarbon group substituted with a protected carboxy group and
$R_{2b}$ is aliphatic hydrocarbon group substituted with carboxy.

The starting compound (III) can be prepared by the methods illustrated below.

Process 1:

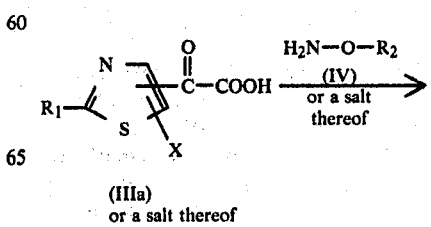

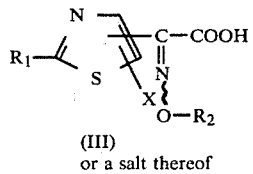

(III)
or a salt thereof

Process 2: Halogenation

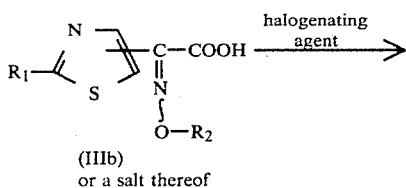

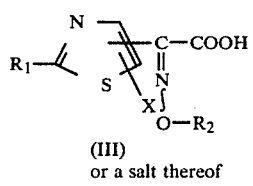

(III)
or a salt thereof

Process 3: Exchange reaction of amino-protective group

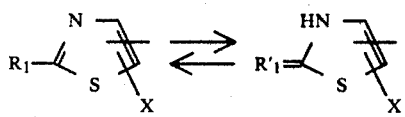

(IIIc)    (IIId)
or a salt thereof    or a salt thereof wherein $R_1$, $R_2$ and X are each as defined above.

$R_{1b}$ is a protected amino group, and $R_{1c}$ is a protected amino group which is different from $R_{1b}$.

The terms and definitions described in this specification are illustrated as follows.

(a) Partial structure of the formula:

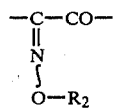

is intended to mean both of the geometric formulae:

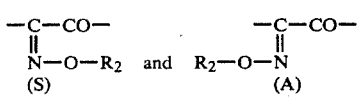

(Wherein $R_2$ is as defined above)

The geometry of the formula (S) is referred to as "syn" and another formula (A) is referred to as "anti." Accordingly, one isomer having the partial structure of the above formula (S) is referred to as "syn isomer" and another isomer having the alternative one of the above formula (A) is referred to as "anti isomer," respectively.

(b) The thiazolyl group of the formula:

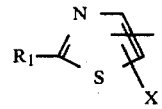

(wherein $R_1$ and X are each as defined above)
is well known to lie in tautomeric relation with a thiazolinyl group of the formula:

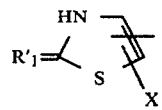

(wherein X is as defined above and $R_1'$ is imino or a protected imino group)

The tautomerism between the said thiazolyl and thiazolinyl groups can be illustrated by the following equilibrium:

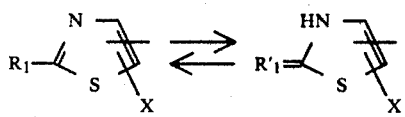

(wherein $R_1$, $R_1'$ and X are each as defined above).

Accordingly, it is to be understood that both of the said groups are substantially the same, and the tautomers consisting of such groups are regarded as the same compounds especially in the manufacturing chemistry. Therefore, both of the tautomeric forms of the compounds having such groups in their molecule are included in the scope of this invention and designated inclusively with one expression "thiazolyl" and represented by the formula:

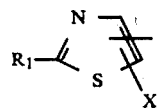

(wherein $R_1$ and X are each as defined above)
only for the convenient sake throughout this specification.

In the above and subsequent descriptions of this specification, suitable examples and illustration of the various definitions which this invention intends to include within the scope thereof are explained in details as follows.

The term "lower" is used to intend a group having 1 to 6 carbon atoms, unless otherwise provided.

"Protective group" in the "protected amino group" may include a conventional N-protective group such as acyl, substituted or unsubstituted ar(lower)alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.), tetrahydropyranyl, substituted phenylthio, substituted alkylidene, substituted aralkylidene, substituted cycloalkylidene, or the like.

Suitable acyl for the N-protective group may be aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s); lower alkoxycarbonyl having 2 to 7 carbon atoms (e.g. methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 2 to 6 carbon atoms; lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.); and the like.

The acyl as stated above may have 1 to 3 suitable substituent(s) sych as halogen (e.g. chlorine, bromine, iodine or fluorine), hydroxy, cyano, nitro, lower alkoxy (e.g. methoxy, ethoxy, propoxy, isopropoxy, etc.), lower alkyl (e.g. methyl, ethyl, propyl, isopropyl, butyl, etc.), lower alkenyl (e.g. vinyl, allyl, etc.), aryl (e.g. pehnyl, tolyl, etc.), or the like.

And further, the reaction product of a silan, boron, aluminium or phosphorus compound with the amino group may also be included in the N-protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

"Halogen" may be chlorine, bromine, iodine or fluorine, and preferred one is chlorine or bromine.

Suitable "aliphatic hydrocarbon group" in the term "aliphatic hydrocarbon group which may have suitable substituent(s)" may be lower alkyl (e.g. methyl, ethyl, propyl, isopropyl, butyl, isobutyl, t-butyl, pentyl, hexyl, etc.), lower alkenyl (e.g. vinyl, 1-propenyl, allyl, 1 or 2 or 3-butenyl, 1 or 2 or 3 or 4-pentenyl, 1 or 2 or 3 or 4 or 5-hexenyl, etc.), lower alkynyl (e.g. ethynyl, 2-propynyl, 1 or 2 or 3-butynyl, 1 or 2 or 3 or 4-pentynyl, 1 or 2 or 3 or 4 or 5-hexynyl, etc.), or the like.

Suitable substituent(s) in the term "aliphatic hydrocarbon group which may have suitable substituent(s)" may be lower alkylthio (e.g. methylthio, ethylthio, propylthio, isopropylthio, butylthio, isobutylthio, t-butylthio, pentylthio, etc.), protected carboxy group as illustrated below, carboxy, or the like.

Suitable "protected carboxy group" may include an esterified carboxy group.

Suitable "ester moiety" in "esterified carboxy group" may include lower alkyl ester (e.g. methyl ester, ethyl ester, propyl ester, isopropyl ester, butyl ester, isobutyl ester, t-butyl ester, pentyl ester, tertpentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester isopropylthiomethyl ester, etc.), amino- and carboxy-substituted-lower alkyl ester (e.g. 2-amino-2-carboxyethyl ester, 3-amino-3-carboxypropyl ester, etc.), protected amino- and protected carboxy-substituted-lower alkyl ester such as lower alkoxycarbonylamino- and mono(or di or tri)phenyl(lower)alkoxycarbonyl-substituted-lower alkyl ester (e.g. 2-tert-butoxycarbonylamino-2-benzhydryloxycarbonylethyl ester, 3-tert-butoxycarbonylamino-3-benzhydryloxycarbonylpropyl ester, etc.), mono(or di or tri)halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 2-acetoxyethyl ester, 2-propionyloxyethyl ester, 1-acetoxypropyl ester, etc.), lower alkanesulfonyl(lower)alkyl ester (e.g. mesylmethyl ester, 2-mesylethyl ester, etc.), ar(lower)alkyl ester which may have one or more substituent(s) such as mono(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)-methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), heterocyclic ester (e.g. phthalidyl ester, etc.), and the like.

The preferable examples of the object compound (I) are exemplified as follows:

Preferable example of $R_1$ is amino or acylamino [more preferably lower alkanoylamino or halo(lower)-alkanoylamino];

$R_2$ is lower alkyl, lower alkynyl, carboxy(lower)alkyl, esterified carboxy(lower)alkyl [more preferably lower alkoxycarbonyl(lower)alkyl], lower alkenyl, or lower alkylthio(lower)alkyl; and X is chlorine or bromine.

Suitable pharmaceutically acceptable salts of the object compound (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

The processes for preparing the object compound (I) are explained in details in the following.

Process A: N-Acylation

A compound (I) or its salt can be prepared by reacting a compound (II) or its reactive derivative at the amino or a salt thereof with a compound (III) or its reactive derivative at the carboxy or a salt thereof according to a conventional manner of so-called amidation reaction well known in β-lactam chemistry.

Suitable reactive derivative at the amino group of the compound (II) may include a conventional reactive derivative as used in a wide variety of amidation reaction, for example, isocyanato, isothiocyanato, a derivative formed by the reaction of a compound (II) with a silyl compound (e.g. trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthaldehyde, furfural, thiophenecarboaldehyde, etc., or the corresponding hydrate, acetal, hemiacetal or enolate thereof), with a ketone compound (e.g. acetone, methyl ethyl ketone, methyl isobutyl ketone, acetylacetone, ethyl acetoacetate, etc., or the corresponding ketal, hemiketal or enolate thereof), with phosphorus compound (e.g. phosphorus oxychloride, phosphorus chloride, etc.), or with a sulfur compound (e.g. thionyl chloride, etc.), and the like.

Suitable salts of the compound (II) may be referred to those as exemplified for the compound (I).

Suitable reactive derivative at the carboxy group of the compound (III) includes conventional ones, for example, an acid halide, an acid anhydride, an activated amide, an activated ester, and the like, and preferable acid halide such as acid chloride, acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

Suitable salts of the compound (III) may include a salt with an inorganic base such as alkali metal salt (e.g. sodium salt, potassium salt, etc.) and an alkaline earth metal salt (e.g. calcium salt, magnesium salt, etc.), a salt with an organic base such as tertiary amine (e.g. trimethylamine salt, triethylamine salt, N,N-dimethylaniline salt, pyridine salt, etc.), a salt with an inorganic acid (e.g. hydrochloride, hydrobromide, etc.) and the like.

The suitable reactive derivatives of the compounds (II) and (III) can be optionally selected from the above according to the kind of the compounds (II) and (III) to be used practically, and to the reaction conditions.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence the reaction, or an optional mixture thereof. The reaction temperature is not critical and the reaction is preferably carried out under cooling to under heating.

When the acylating agent (III) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.); a bisimidazolide compound (e.g. N,N'-carbonylbis(2-methylimidazole), etc.); an imine compound (e.g. pentamethyleneketene-N-cyclohexylimine, diphenylketene-N-cyclohexylimine, etc.); an olefinic or acetylenic ether compound (e.g. ethoxyacetylene, β-chlorovinylethyl ether, etc.); 1-(4-chlorobenzenesulfonyloxy)-6-chloro-1H-benzotriazole; N-ethylbenzisoxazolium salt; N-ethyl-5-phenylisoxazolium-3'-sulfonate; a phosphorus compound (e.g. polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.); thionyl chloride; oxalyl chloride; Vilsmeier reagent prepared by the reaction of N,N-dimethylformamide with thionyl chloride, phosphorus oxychloride or phosgene; or the like.

The object compound (I) and salt thereof are useful as an antimicrobial agent, and a part thereof can also be used as a starting material in the following processes.

Process B: Elimination of amino-protective group

A compound (Ia) or a salt thereof can be prepared by subjecting a compound (Ia') or a salt thereof to elimination reaction of the protective group of amino.

The elimination reaction may be conducted in accordance with a conventional method such as hydrolysis, reduction or the like. These methods may be selected according to the kind of the protective group to be eliminated.

The hydrolysis may include a method using an acid (acidic hydrolysis), a base (basis hydrolysis) or hydrazine, and the like.

Among these methods, hydrolysis using an acid is one of the common and preferable methods for eliminating the protective group such as an acyl group, for example, substituted or unsubstituted lower alkanoyl, substituted or unsubstituted lower alkoxycarbonyl, substituted or unsubstituted ar(lower)alkoxycarbonyl, lower cycloalkoxycarbonyl, substituted phenylthio, substituted alkylidene, substituted aralkylidene, substituted cycloalkylidene or the like. Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can easily be separated out from the reaction product by a conventional manner such as neutralization or distillation under reduced pressure, for example, formic acid, trifluoroacetic acid, hydrochloric acid or the like. The acid suitable for the reaction can be selected in consideration of the chemical property of the starting compound (Ia') and the product (Ia) as well as the kind of the protective group to be eliminated. The acidic hydrolysis can be conducted in the presence or absence of a solvent. Suitable solvent may be a conventional organic solvent, water or a mixture thereof, which does not adversely influence this reaction.

The hydrolysis using a base can be applied for eliminating the protective group such as an acyl group, preferably, for example, haloalkanoyl (e.g. trifluoroacetyl, etc.) and the like. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as alkali metal acetate (e.g. sodium acetate, potassium acetate, etc.), trialkylamine (e.g. trimethylamine, triethylamine, etc.), picoline, N-methylpyrrolidine, N-methylmorpholine, 1,5-diazabicyclo[4,3,0]-5-nonene, 1,4-diazabicyclo[2,2,2]-octane, 1,5-diazabicyclo[5,4,0]-7-undecene, anionexchange resin or the like. The hydrolysis using a base is often carried out in water or a conventional organic solvent or a mixture thereof.

The hydrolysis using hydrazine can be applied for eliminating the protective group such as dibasic acyl, for example, succinyl, phthaloyl or the like.

The reduction can be applied for eliminating the protective group such as acyl, for example, halo(lower)alkoxycarbonyl (e.g. trichloroethoxycarbonyl, etc.), substituted or unsubstituted ar(lower)alkoxycarbonyl (e.g. benzyloxycarbonyl, p-nitrobenzyloxycarbonyl, etc.), 2-pyridylmethoxycarbonyl, etc., aralkyl (e.g. benzyl, benzhydryl, trityl, etc.) and the like. Suitable reduction may include, for example, reduction using an alkali metal borohydride (e.g. sodium borohydride, etc.), conventional catalytic hydrogenolysis and the like.

And further, the protective group such as halo(lower)alkoxycarbonyl or 8-quinolyloxycarbonyl can be eliminated by treatment with a heavy metal such as copper, zinc or the like.

The reaction temperature is not critical and may optionally be selected in consideration of the chemical property of the starting compound and reaction product as well as the kind of the N-protective group and the method to be applied, and the reaction is preferably carried out under a mild condition such as under cooling, at ambient temperature or slightly elevated temperature.

Process C: Elimination of carboxy-protective group

The object compound (Ib) or a salt thereof can be prepared by subjecting the compound (Ib') or a salt thereof to elimination reaction of the protective group of carboxy.

The present invention is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]-none-5-ene, 1,4-diazabicyclo[2,2,2]octane, 1,8-diazabicyclo[5,4,0]undecene-7, or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.). The acidic hydrolysis using trifluoroacetic acid is usually accelerated by addition of anisole.

The reaction is usually carried out in a solvent such as water, methylene chloride, an alcohol (e.g. methanol, ethanol, etc.), a mixture thereof or any other solvent which does not adversely influence to the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

The processes for the preparation of the starting compounds are explained in details in the following.

Process 1:

The compound (III) or a salt thereof can be prepared by reacting the compound (IIIa) or a salt thereof with the compound (IV) or a salt thereof.

Suitable salts of the compound (IV) may include the same acid addition salts as exemplified for the compound (I).

Suitable salts of the compound (IIIa) may include the same ones as exemplified for the compound (III).

In this reaction, when the compound (IV) is used in a salt form, this reaction can also be carried out in the presence of a base such as alkali metal (e.g. lithium, sodium, potassium etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, etc.), quinoline, and the like.

The reaction is usually carried out in a conventional solvent which does not adversely influence the reaction such as water, methanol, ethanol, propanol, dioxane, tetrahydrofuran, etc., or a mixture thereof.

The reaction temperature is not critical and the reaction is usually carried out under cooling to heating.

Process 2:

The compound (III) or a salt thereof can be prepared by reacting the compound (IIIb) or a salt thereof with halogenating agent.

Suitable halogenating agent may include a conventional halogenating agent such as chlorine, bromine, N-chlorosuccinimide, N-bromosuccinimide, trichloroisocyanuric acid and the like.

Suitable salts of the compound (IIIb) may include the same ones as exemplified for the compound (III).

The reaction is usually conducted in a solvent such as chloroform, acetic acid, methylenechloride, dichloroethane or any other solvent which does not adversely influence the reaction. The reaction temperature is not critical and the reaction is preferably carried out under cooling to under heating.

Process 3: Exchange reaction of amino-protective group

The compound (IIId) or a salt thereof can be prepared by subjecting the compound (IIIc) or a salt thereof to exchange reaction of amino-protective group in accordance with a conventional method.

Suitable salts of the compounds (IIIc) and (IIId) may include the same ones as exemplified for the compound (III).

The reagent to be used in this reaction may include a conventional acylating agent such as the corresponding acid to the acyl group as aforementioned or its reactive derivative as mentioned above.

In order to show the utility of the object compound (I), the test data of representative compound are shown in the following.

In vitro antibacterial activity (1) Test method:

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of μg/ml after incubation at 37° C. for 20 hours.

(2) Test compound:

7-[2-ethoxyimino-2-(2-amino-5-chlorothiazol-4-yl)acetamido]-3-(1-pyridiniomethyl)-3-cephem-4-carboxylate (syn isomer).

(3) Test results:

| Test Bacteria | M.I.C. (μg/ml) |
|---|---|
| P. aeruginosa 2 | 12.50 |
| C. freundii 75 | 3.13 |

For prophylactic and/or therapeutic administration, the compound (I) of the present invention is used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age and conditions of the patient, a kind of disease and a degree of the infection, and further a kind of the compound (I) to be applied, etc., an average single dose of about 50 mg, 100 mg, 250 mg, and 500 mg of the compound (I) is sufficient for treating infectious diseases caused by pathogenic bacteria. In general, the compound (I) can be administered in an amount between 1 mg/kg and 100 mg/kg, preferably 5 mg/kg and 50 mg/kg.

Following Preparations and Examples are given for explaining this invention in more detail.

Preparation 1

A solution of hydrazine hydrate (2.3 g) in methanol (2.3 g) was added to a mixture of N-(methylthiomethoxy) phthalimide (10.2 g) in tetrahydrofuran (30 ml) and stirred at ambient temperature for 30 minutes. 10% Hydrochloric acid (18 ml) was added to the reaction mixture under ice-cooling and the insoluble materials were filtered off to give a solution containing methylthiomethoxyamine. On the other hand, ethyl (2-formamido-5-chlorothiazol-4-yl)glyoxylate (10 g) was added to the 1 N aqueous potassium hydroxide (76.2 ml) at ambient temperature and the mixture was stirred for 10 minutes. The reaction mixture was adjusted to pH 2.0 with 10% hydrochloric acid under ice-cooling, thereto were added pyridine (10 g) and the above solution containing methylthiomethoxyamine, followed by stirring at ambient temperature for 3 hours. The aqueous solution was adjusted to pH 7.5 with 10% aqueous potassium hydroxide and washed with ethyl acetate. Ethyl acetate was added to the aqueous solution and the resulting mixture was adjusted to pH 1.7 with 10% hydrochloric acid, and the separated organic layer was washed with 3% hydrochloric acid and water, dried over magnesium sulfate and evaporated to give 2-methylthiomethoxyimino-2-(2-formamido-5-chlorothiazol-4-yl)acetic acid (syn isomer)(8.1 g).

IR (Nujol): 3175, 1760 (sh), 1740, 1640, 1615 cm$^{-1}$.

NMR (DMSO-d$_6$, δ): 2.25 (3H, s), 5.35 (2H, s), 8.57 (1H, s), 12.97 (1H, broad s).

Preparation 2

Ethyl (2-formamido-5-chlorothiazol-4-yl)glyoxylate (14.5 g) was added to a solution of 1 N aqueous potassium hydroxide (110 ml) at ambient temperature, and the mixture was stirred for 10 minutes to prepare the solution of potassium (2-formamido-5-chlorothiazol-4-yl)glyoxylate. After this solution was adjusted to pH 2 with 10% hydrochloric acid under ice-cooling, thereto were added pyridine (20 ml) and a solution of tert-butyl 2-aminooxyacetate (10.3 g) in tetrahydrofuran (50 ml), followed by stirring at ambient temperature for 5 hours. After the reaction mixture was washed with ethyl acetate, the remaining aqueous solution was adjusted to pH 1.5 with 10% hydrochloric acid and extracted with ethyl acetate. The extract was washed with an aqueous sodium chloride and then dried over magnesium sulfate. Removal of the solvent gave 2-tert-butoxycarbonylmethoxyimino-2-(2-formamido-5-chlorothiazol-4-yl)acetic acid (syn isomer)(8.5 g).

IR (Nujol): 3150, 1725, 1690, 1650, 1560, 1530 cm$^{-1}$.

NMR (DMSO-d$_6$, δ): 1.47 (9H, s), 4.75 (2H, s), 8.7 (1H, s), 12.8 (1H, s).

Preparation 3

A solution of chlorine (3.2 g) in acetic acid (44 ml) was added dropwise to a solution of 2-(2-propynyloxyimino)-2-(2-formamidothiazol-4-yl)acetic acid (syn isomer)(10 g) in chloroform (250 ml) at 0° C. and the mixture was stirred for 30 minutes at the same temperature. The resulting solution was added to a saturated aqueous sodium bicarbonate and the mixture was adjusted to pH 7.5 with 10% aqueous sodium hydroxide. The separated aqueous layer was adjusted to pH 2.0 with conc. hydrochloric acid and extracted with ethyl acetate. The extracts were washed with a saturated aqueous sodium chloride, dried over magnesium sulfate and evaporated. The residue was washed with diisopropyl ether and filtered to give 2-(2-propynyloxyimino)-2-(2-formamido-5-chlorothiazol-4-yl)acetic acid (syn isomer)(5.96 g), mp 161°-162° C. (dec.).

IR (Nujol): 3280, 3120, 2120, 1730, 1690, 1650 cm$^{-1}$.

NMR (DMSO-d$_6$, δ): 3.53 (1H, m), 4.86 (2H, d, J=2.0 Hz), 8.58 (1H, s), 12.97 (1H, broad s).

Preparation 4

The following compound was prepared according to the similar manner to that of Preparation 3. 2-Ethoxyimino-2-(2-formamido-5-chlorothiazol-4-yl)-acetic acid (syn isomer), mp 164°–165° C. (dec.).

IR (Nujol): 3170, 1750, 1730, 1700, 1650 cm$^{-1}$

NMR (DMSO-d$_6$, δ): 1.27 (3H, t, J=7.0 Hz), 4.22 (2H, q, J=7.0 Hz), 8.56 (1H, s), 12.97 (1H, broad s)

Preparation 5

Ethyl (2-formamido-5-chlorothiazol-4-yl)glyoxylate (40.0 g) was added to 1 N aqueous solution of potassium hydroxide (305 ml) at ambient temperature and stirred for 10 minutes. The reaction mixture was adjusted to pH 2.0 with 10% aqueous hydrochloric acid under ice cooling. A solution of allyloxyamine (14.4 g) in tetrahydrofuran (200 ml) was added to the stirred suspension of the above mixture in pyridine (54.1 g) at ambient temperature and stirred for 4 hours at the same temperature. The resultant mixture was adjusted to pH 7.5 with a saturated aqueous solution of sodium bicarbonate, and washed with ethyl acetate. The separated aqueous layer was adjusted to pH 2.0 with 10% hydrochloric acid and extracted with ethyl acetate. The extract was washed with a saturated aqueous solution of sodium chloride, dried over magnesium sulfate and evaporated under reduced pressure. The residue was washed with diisopropyl ether and collected by filtration to give 2-allyloxyimino-2-(2-formamido-5-chlorothiazol-4-yl)acetic acid (syn isomer) (24.74 g), mp. 166° to 167° C.

IR (Nujol): 3140, 1730, 1695, 1650 cm$^{-1}$. NMR (DMSO-d$_6$, δ): 4.69 (2H, m), 5.09–5.59 (2H, m), 5.67–6.41 (1H, m), 8.52 (1H, s), 12.87 (1H, broad s).

Preparation 6

2,2,2-Trifluoroacetic anhydride (21.5 ml) and triethylamine (21.2 ml) were added to the stirred suspension of 2-allyloxyimino-2-(2-formamido-5-chlorothiazol-4-yl)acetic acid (syn isomer) (20.0 g) in tetrahydrofuran (110 ml) at −10° to −5° C. and the mixture was stirred for 2 hours at 0° to 5° C. The reaction mixture was poured into a mixture of ethyl acetate and water, and the resultant mixture was adjusted to pH 7.5 with 10% aqueous solution of sodium hydroxide. The separated aqueous layer was adjusted to pH 2.5 with 10% hydrochloric acid and extracted with ethyl acetate. The ethyl acetate layer was washed with brine, dried over magnesium sulfate and evaporated to give 2-allyloxyimino-2-[2-(2,2,2-trifluoroacetamido)-5-chlorothiazol-4-yl]acetic acid (syn isomer) (14.18 g). m.p. 162° C. (dec.).

IR (Nujol): 1720 cm$^{-1}$.

NMR (DMSO-d$_6$, δ): 4.72 (2H, d, J=6.0 Hz), 5.11–5.61 (2H, m), 5.73–6.43 (1H, m).

EXAMPLE 1

Vilsmeier reagent was prepared from phosphorous oxychloride (2.0 g) and N,N-dimethylformamide (0.95 g) in tetrahydrofuran (2 ml) in a usual manner. 2-(Methylthiomethoxyimino)-2-(2-formamido-5-chlorothiazol-4-yl)acetic acid (syn isomer) (3.4 g) was added to the stirred suspension of Vilsmeier reagent in ethyl acetate (30 ml) under ice-cooling and the mixture was stirred for 30 minutes at the same temperature to produce an activated acid solution. On the other hand, 1-[(7-amino-4-carboxy-3-cephem-3-yl)methyl]-pyridinium chloride hydrochloride dihydrate (4 g) was dissolved in a solution of trimethylsilylacetamide (13.1 g) in tetrahydrofuran (80 ml). To a solution was added the above activated acid solution at 0° C. and the mixture was stirred at 0° to 5° C. for 30 minutes. Water (70 ml) and ethyl acetate (300 ml) was added to the reaction mixture at 0° C., and separated aqueous layer was washed with ethyl acetate.

The aqueous layer was adjusted to pH 4.0 with 10% aqueous sodium hydroxide under ice-cooling. The solution was subjected to column chromatography on macroporus non-ionic adsorption resin "Diaion HP-20" (Trademark: Prepared by Mitsubishi Chemical Industries) and eluted with 20% aqueous solution of isopropyl alcohol. The fractions containing the object compound were collected and concentrated and lyophilized to give 7-[2-methylthiomethoxyimino-2-(2-formamido-5-chlorothiazol-4-yl)acetamido]-3-(1-pyridiniomethyl)-3-cephem-4-carboxylate (syn isomer) (2.92 g).

IR (Nujol): 3300 (broad), 1775, 1670, 1620 cm$^{-1}$

NMR (DMSO-d$_6$, δ): 2.22 (3H, s), 3.40 (2H, q, J=17 Hz), 5.12 (1H, d, J=5 Hz), 5.23 (2H, s), 5.20–5.92 (2H, m), 5.80 (1H, dd, J=5 Hz, 8 Hz), 8.17 (2H, dd, J=6 Hz, 6 Hz), 8.53 (1H, s), 8.63 (1H, m), 9.40 (2H, d, J=6 Hz), 9.67 (1H, d, J=8 Hz).

EXAMPLE 2

Vilsmeier reagent was prepared from phosphorous oxychloride (2.5 g) and N,N-dimethylformamide (1.2 g) in ethyl acetate (4.8 ml) in a usual manner. 2-(t-Butoxycarbonylmethoxyimino)-2-(2-formamido-5-chlorothiazol-4-yl)acetic acid (syn isomer) (5.0 g) was added to the stirred suspension of Vilsmeier reagent in tetrahydrofuran (70 ml) under ice-cooling, and stirred for 30 minutes at the same temperature to produce an activated acid solution. Trimethylsilylacetamide (16.4 g) was added to the stirred suspension of 1-[(7-amino-4-carboxy-3-cephem-3-yl)methyl]pyridinium chloride hydrochloride dihydrate (5.0 g) in tetrahydrofuran (100 ml). To the solution was added the above activated acid solution at −10° C. and stirred at −10° C.–5° C. for 40 minutes. A saturated aqueous sodium chloride was added to the reaction mixture and adjusted to pH 3.0 with 10% aqueous sodium hydroxide. The separated aqueous layer was extracted three times with tetrahydrofuran. The organic layer was washed with a little saturated aqueous sodium chloride, dried over magnesium sulfate and evaporated to give 7-[2-t-butoxycarbonylmethoxyimino-2-(2-formamido-5-chlorothiazol-4-yl)acetamido]-3-(1-pyridiniomethyl)-3-cephem-4-carboxylate (syn isomer) (2.13 g).

IR (Nujol): 1770, 1730, 1670, 1630 cm$^{-1}$.

EXAMPLE 3

The following compounds were prepared according to the similar manners to those of Examples 1 and 2.

(1) 7-[2-(Ethoxyimino-2-[2-formamido-5-chlorothiazol-4-yl)acetamido]-3-(1-pyridiniomethyl)-3-cephem-4-carboxylate (syn isomer).

IR (Nujol): 1775, 1670, 1610 cm$^{-1}$.

NMR (DMSO-d$_6$, δ): 1.24 (3H, t, J=7.0 Hz), 3.09, 3.62 (2H, q, J=18.0 Hz), 4.14 (2H, q, J=7.0 Hz), 5.09 (1H, d, J=5.0 Hz), 5.06–5.92 (2H, m), 5.72 (1H, dd, J=5.0 Hz, 8.0 Hz), 8.17 (2H, dd, J=6.0 Hz), 8.54 (1H, s), 8.62 (1H, m), 9.33–9.73 (3H, m).

(2) 7-[2-(2-Propynyloxyimino)-2-(2-formamido-5-chlorothiazol-4-yl)acetamido]-3-(1-pyridiniomethyl)-3-cephem-4-carboxylate (syn isomer).

IR (Nujol): 3250, 2130, 1780, 1670, 1610 cm$^{-1}$

NMR (DMSO-d$_6$, δ): 2.82–3.93 (2H, m), 3.46 (1H, m), 4.72 (2H, m), 5.07 (1H, d, J=5.0 Hz), 5.31 (2H, q, J=14.0 Hz), 5.69 C1H, dd, J=5.0 Hz, 8.0 Hz), 8.14 (2H, m), 8.53 (2H, m), 9.30–9.76 (3H, m).

(3) 7-[2-Methylthiomethoxyimino-2-(2-amino-5-chlorothiazol-4-yl)acetamido]-3-(1-pyridiniomethyl)-3-cephem-4-carboxylate (syn isomer).

IR (Nujol): 3300, 1770, 1660, 1610, 1530 cm$^{-1}$.

(4) 7-[2-t-Butoxycarbonylmethoxyimino-2-(2-amino-5-chlorothiazol-4-yl)acetamido]-3-(1-pyridiniomethyl)-3-cephem-4-carboxylate (syn isomer).

NMR (DMSO-d$_6$, δ): 1.41 (9H, s), 3.39 (2H, m), 4.52 (2H, s), 5.13 (1H, d, J=5.0 Hz), 5.12–5.92 (2H, m), 5.77 (1H, dd, J=5.0 Hz, 8.0 Hz), 7.46 (2H, broad s), 8.24 (2H, m), 8.68 (1H, m), 9.26–9.58 (3H, m).

(5) 7-[2-Carboxymethoxyimino-2-(2-amino-5-chlorothiazol-4-yl)acetamido]-3-(1-pyridiniomethyl)-3-cephem-4-carboxylate (syn isomer).

IR (Nujol): 3300, 3170, 1770, 1660, 1610 cm$^{-1}$.

(6) 7-[2-(2-Propynyloxyimino)-2-(2-amino-5-chlorothiazol-4-yl)acetamido]-3-(1-pyridiniomethyl)-3-cephem-4-carboxylate (syn isomer).

IR (Nujol): 3280, 1775, 1665, 1610 cm$^{-1}$.

(7) 7-[2-Ethoxyimino-2-(2-amino-5-chlorolthiazol-4-yl)acetamido]-3-(1-pyridiniomethyl)-3-cephem-4-carboxylate (syn isomer).

IR (Nujol): 3290, 3190, 1775, 1660, 1610 cm$^{-1}$.

(8) 7-[2-Allyloxyimino-2-(2-amino-5-chlorothiazol-4-yl)-acetamido]-3-(1-pyridiniomethyl)-3-cephem-4-carboxylate (syn isomer).

IR (Nujol): 3280, 3180, 1770, 1660, 1610 cm$^{-1}$.

EXAMPLE 4

Conc. hydrochloric acid (1.5 g) was added to the mixture of 7-[2-methylthiomethoxyimino-2-(2-formamido-5-chlorothiazol-4-yl)acetamido]-3-(1-pyridiniomethyl)-3-cephem-4-carboxylate (syn isomer) (2.8 g) and methanol (30 ml), and stirred at ambient temperature for 5 hours. After removal of solvent, and the residue was dissolved in water and the solution was adjusted to pH 4.0 with 10% aqueous sodium hydroxide under ice-cooling. The solution was subjected to column chromatography on macroporus non-ionic adsorption resin "Diaion HP-20" and eluted with 20% aqueous solution of isopropyl alcohol. The fractions containing the object compound were collected and concentrated and lyophilized to give 7-[2-methylthiomethoxyimino-2-(2-amino-5-chlorothiazol-4-yl)acetamido]-3-(1-pyridiniomethyl)-3-cephem-4-carboxylate (syn isomer) (1.7 g).

IR (Nujol): 3300, 1770, 1660, 1610, 1530 cm$^{-1}$.

NMR (DMSO-d$_6$+D$_2$O, δ): 2.20 (3H, s), 3.35 (2H, q, J=18 Hz), 5.12 (1H, d, J=5 Hz), 5.20 (2H, s), 5.30 (2H, q, J=13 Hz), 5.72 (1H, d, J=5 Hz), 8.15 (2H, m), 8.57 (1H, m), 9.28 (2H, d, J=5 Hz).

EXAMPLE 5

The following compounds were prepared according to the similar manner to that of Example 4.

(1) 7-[2-t-Butoxycarbonylmethoxyimino-2-(2-amino-5-chlorothiazol-4-yl)acetamido]-3-(1-pyridiniomethyl)-3-cephem-4-carboxylate (syn isomer).

NMR (DMSO-d$_6$, δ): 1.41 (9H, s), 3.39 (2H, m), 4.52 (2H, s), 5.13 (1H, d, J=5.0 Hz), 5.12–5.92 (2H, m), 5.77 (1H, dd, J=5.0 Hz, 8.0 Hz), 7.46 (2H, broad s), 8.24 (2H, m), (2) 7-[2-Ethoxyimino-2-(2-amino-5-chlorothiazol-4-yl)acetamido]-3-(1-pyridiniomethyl)-3-cephem-4-carboxylate (syn isomer).

IR (Nujol): 3290, 3190, 1775, 1660, 1610 cm$^{-1}$.

NMR (D$_2$O, δ): 1.32 (3H, t, J=7.0 Hz), 3.17, 3.70 (2H, q, J=18.0 Hz), 4.28 (2H, q, J=7.0 Hz), 5.27 (1H, d, J=5.0 Hz), 5.49 (2H, m), 5.87 (1H, d, J=5.0 Hz), 8.11 (2H, dd, J=6.0 Hz), 8.60 (1H, m), 8.98 (2H, d, J=6.0 Hz).

(3) 7-[2-Carboxymethoxyimino-2-(2-amino-5-chlorothiazol-4-yl)-acetamido]-3-(1-pyridiniomethyl)-3-cephem-4-carboxylate (syn isomer) (0.97 g).

IR (Nujol): 3300, 3170, 1770, 1660, 1610 cm$^{-1}$.

(4) 7-[2-(2-Propynyloxyimino)-2-(2-amino-5-chlorothiazol-4-yl)acetamido]-3-(1-pyridiniomethyl)-3-cephem-4-carboxylate (syn isomer).

IR (Nujol): 3280, 1775, 1665, 1610 cm$^{-1}$.

NMR (D$_2$O, δ): 2.99 (1H, m), 3.19, 3.69 (2H, q, J=16.0 Hz), 4.84 (2H, m), 5.27 (1H, d, J=5.0 Hz), 5.50 (2H, m), 5.87 (1H, d, J=5.0 Hz), 8.16 (2H, dd, J=6.0 Hz), 8.61 (1H, m), 8.98 (2H, d, J=6.0 Hz).

EXAMPLE 6

Trifluoroacetic acid (11.2 ml) was added to a solution of 7-[2-t-butoxycarbonylmethoxyimino-2-(2-amino-5-chlorothiazol-4-yl)acetamido]-3-(1-pyridiniomethyl)-3-cephem-4-carboxylate (syn isomer) (2.8 g) in methylene chloride (6 ml) and anisole (2.8 ml) under ice-cooling, and the mixture was stirred for an hour at ambient temperature. The reaction mixture was added to diisopropyl ether (120 ml) and precipitates were filtered. The precipitates were added to water and adjusted to pH 4.0 with 10% aqueous sodium hydroxide. The resulting solution was subjected to column chromatography on macroporus non-ionic adsorption "Diaion HP-20" and eluted with 15% aqueous solution of isopropyl alcohol. The fractions containing the object compound were collected and concentrated and lyophilized to give 7-[2-carboxymethoxyimino-2-(2-amino-5-chlorothiazol-4-yl)acetamido]-3-(1-pyridiniomethyl)-3-cephem-4-carboxylate (syn isomer) (0.97 g).

IR (Nujol): 3300, 3170, 1770, 1660, 1610 cm$^{-1}$.

NMR (D$_2$O, δ): 3.19 and 3.66 (2H, q, J=18.0 Hz), 4.40–5.00 (2H, over lapped with H$_2$O), 5.29 (1H, d, J=4.0 Hz), 5.51 (2H, q, J=14.0 Hz), 5.93 (1H, d, J=4.0 Hz), 8.11 (2H, dd, J=6.0 Hz), 8.59 (1H, m), 9.00 (2H, d, J=6.0 Hz).

EXAMPLE 7

(1) Vilsmeier reagent was prepared from phosphorus oxychloride (2.0 g) and N,N-dimethylformamide (0.95 g) in ethyl acetate (3.8 ml) in a usual manner. 2-Allyloxyimino-2-[2-(2,2,2-trifluoroacetamido)-5-chlorothiazol-4-yl]acetic acid (syn isomer) (3.9 g) was added to the stirred suspension of Vilsmeier reagent in methylene chloride (40 ml) under ice-cooling and stirred for 20 minutes at the same temperature to produce an activated solution. On the other hand, trimethylsilylacetamide (13.1 g) was added to the stirred suspension of 1-[(7-amino-4-carboxy-3-cephem-3-yl)methyl]-pyridinium chloride hydrochloride dihydrate (4.0 g) in methylene chloride (80 ml) and the mixture was stirred for 15 minutes at 38° to 43° C. To the resultant solution was added the above activated solution at −10° C. and the mixture was stirred for 30 minutes at the same temperature. Water (70 ml) was added to the reaction mixture. The aqueous layer was separated out, and then the resultant organic layer was extracted with water (30 ml). The combined aqueous layer was adjusted to pH 4.0 with 10% aqueous solution of sodium hydroxide to give an aqueous solution containing 7-[2-allyloxyimino-2-{2-(2,2,2-trifluoroacetamido)-5-chlorothiazol-4-yl}acetamido]-3-(1-pyridiniomethyl)-3-cephem-4-carboxylate (syn isomer).

(2) To an aqueous solution containing 7-[2-allyloxyimino-2-{2-(2,2,2-trifluoroacetamido)-5-chlorothiazol-4-yl}acetamido]-3-(1-pyridiniomethyl)-3-cephem-4-carboxylate (syn isomer) (prepared in Example 7(1)) was added sodium acetate trihydrate (13.6 g). After stirring for 17 hours at ambient temperature and the resultant solution was adjusted to pH 4.0 with 10% hydrochloric acid.

The solution was subjected to column chromatography on macroporous non-ionic adsorption resin "Diaion HP-20" and eluted with 20% aqueous solution of isopropyl alcohol. The fractions containing the object compound was concentrated and lyophilized to give 7-[2-allyloxyimino-2-(2-amino-5-chlorothiazol-4-yl)acetamido]-3-(1-pyridiniomethyl)-3-cephem-4-carboxylate (syn isomer) (1.71 g).

IR (Nujol): 3280, 3180, 1770, 1660, 1610 cm$^{-1}$.

NMR (DMSO-d$_6$, δ): 3.04 and 3.57 (2H, q, J=18.0 Hz) 4.57 (2H, m), 5.06 (1H, d, J=4.0 Hz), 5.00–6.35 (6H, m), 7.33 (2H, broad s), 8.14 (2H, dd, J=6.0 Hz), 8.52 (1H, m), 9.31–9.66 (3H, m).

What we claim is:

1. A compound of the formula:

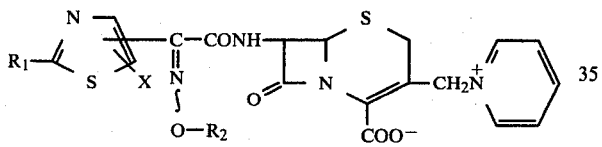

wherein
R$_1$ is amino, lower alkanoylamino or halo(lower)alkanoylamino,
R$_2$ is lower alkyl, lower alkylthio(lower)alkyl, lower alkenyl, lower alkynyl, carboxy(lower)alkyl or esterified carboxy(lower)alkyl, and X is halogen;
and pharmaceutically acceptable salts thereof.

2. Syn isomer of a compound of claim 1, wherein

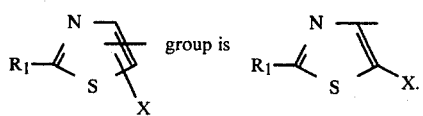

3. A compound of claim 2, wherein
R$_2$ is lower alkyl, lower alkylthio(lower)alkyl, lower alkenyl, lower alkynyl, carboxy(lower)alkyl or lower alkoxycarbonyl(lower)alkyl.

4. A compound of claim 3, wherein
R$_1$ is amino, formamido or 2,2,2-trifluoroacetamido,
R$_2$ is ethyl, methylthiomethyl, allyl, 2-propynyl, carboxymethyl or t-butoxycarbonylmethyl, and
X is chlorine.

5. A compound of claim 4, which is selected from the group consisting of:
7-[2-ethoxyimino-2-(2-amino-5-chlorothiazol-4-yl)acetamido]-3-(1-pyridiniomethyl)-3-cephem-4-carboxylate (syn isomer),
7-[2-methylthiomethoxyimino-2-(2-amino-5-chlorothiazol-4-yl)acetamido]-3-(1-pyridiniomethyl)-3-cephem-4-carboxylate (syn isomer),
7-[2-allyloxyimino-2-(2-amino-5-chlorothiazol-4-yl)-acetamido]-3-(1-pyridiniomethyl)-3-cephem-4-carboxylate (syn isomer),
7-[2-(2-propynyloxyimino)-2-(2-amino-5-chlorothiazol-4-yl)acetamido]-3-(1-pyridiniomethyl)-3-cephem-4-carboxylate (syn isomer),
7-[2-t-butoxycarbonylmethoxyimino-2-(2-amino-5-chlorothiazol-4-yl)acetamido]-3-(1-pyridiniomethyl)-3-cephem-4-carboxylate (syn isomer) and
7-[2-carboxymethoxyimino-2-(2-amino-5-chlorothiazol-4-yl)acetamido]-3-(1-pyridiniomethyl)-3-cephem-4-carboxylate (syn isomer).

6. A pharmaceutical composition comprising, as an antibacterially effective amount of active ingredient, an effective amount of the compound of claim 1, in association with a non-toxic, pharmaceutically acceptable carrier or excipient.

* * * * *

Notice of Adverse Decision in Interference

In Interference No. 101,432, involving Patent No. 4,427,677, T. Takaya, H. Takasugi, M. Murata and A. Yoshioka, CEPHEM COMPOUNDS, final judgment adverse to the patentees was rendered Jan. 24, 1986, as to claims 1–6.
[*Official Gazette April 8, 1986.*]